US006375661B2

(12) United States Patent
Chu et al.

(10) Patent No.: US 6,375,661 B2
(45) Date of Patent: *Apr. 23, 2002

(54) APPARATUS FOR SEVERING AND CAPTURING POLYPS

(75) Inventors: Michael S. H. Chu, Brookline; Yem Chin, Burlington, both of MA (US)

(73) Assignee: Boston Scientific Corporation, Natick, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/730,771

(22) Filed: Dec. 7, 2000

Related U.S. Application Data

(60) Continuation of application No. 09/457,700, filed on Dec. 9, 1999, now Pat. No. 6,171,315, which is a division of application No. 09/146,105, filed on Sep. 3, 1998, now Pat. No. 6,010,512, which is a division of application No. 08/421,409, filed on Apr. 13, 1995, now Pat. No. 5,846,248.

(51) Int. Cl.[7] .............................................. A61B 17/32
(52) U.S. Cl. ...................................... 606/113; 606/114
(58) Field of Search ................................ 606/113, 114, 606/46, 110, 47

(56) References Cited

U.S. PATENT DOCUMENTS

| 3,791,387 A | 2/1974 | Itoh |
| 4,222,380 A | 9/1980 | Terayama |
| 4,326,530 A | 4/1982 | Fleury, Jr. |
| 4,509,517 A | 4/1985 | Zibelin |
| 4,598,699 A | 7/1986 | Garren et al. |
| 4,807,626 A | 2/1989 | McGirr |
| 5,122,147 A | 6/1992 | Sewell, Jr. |
| 5,171,233 A | 12/1992 | Amplatz et al. |
| 5,176,688 A | 1/1993 | Narayan et al. |
| 5,336,227 A | 8/1994 | Nakao et al. |
| 5,376,094 A | 12/1994 | Kline |
| 5,417,697 A | 5/1995 | Wilk et al. |
| 5,542,948 A | 8/1996 | Weaver et al. |
| 5,746,747 A | 5/1998 | McKeating |
| 5,906,620 A | 5/1999 | Nakao et al. |

FOREIGN PATENT DOCUMENTS

DE 25 40 818 4/1976

*Primary Examiner*—Michael H. Thaler
(74) *Attorney, Agent, or Firm*—Finnegan, Henderson, Farabow, Garrett & Dunner, LLP

(57) ABSTRACT

A method and apparatus for managing polyps by which an elongated tubular member is generally positionable within the working channel of an endoscopic device. The tubular member carries a selectively extendable severing device and capturing device at its distal end. Control apparatus at the proximal end of the tubular member enables a physician to extend and retract the severing and capturing devices. The physician retracts the capturing device to grasp the portion of the polyp to be severed and retracts the severing device to sever the polyp. The capturing device retains the severed portion of the polyp for removal with the tubular member. In one embodiment, the capturing device includes an injection needle.

10 Claims, 7 Drawing Sheets

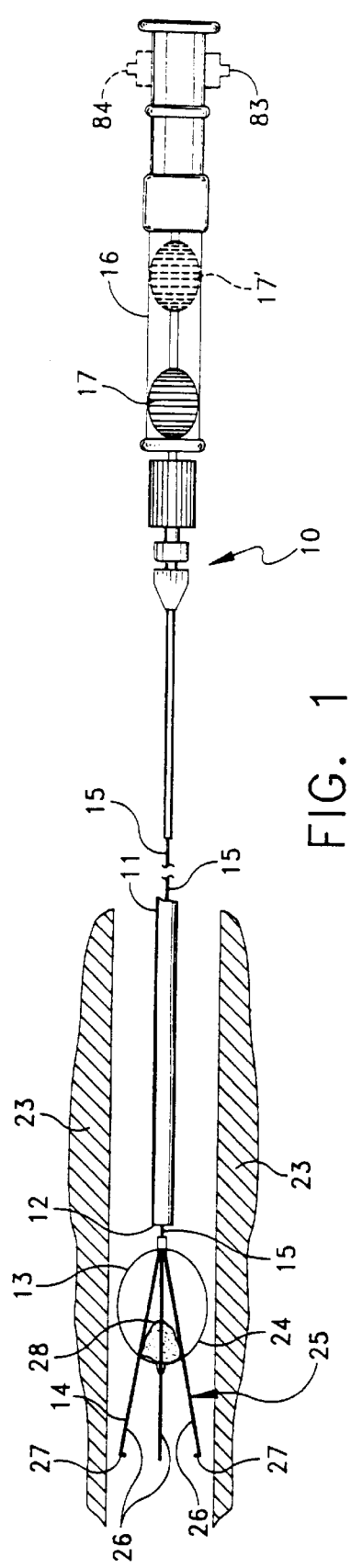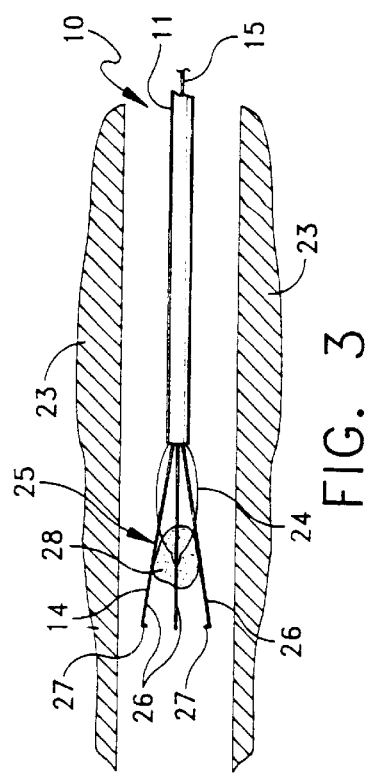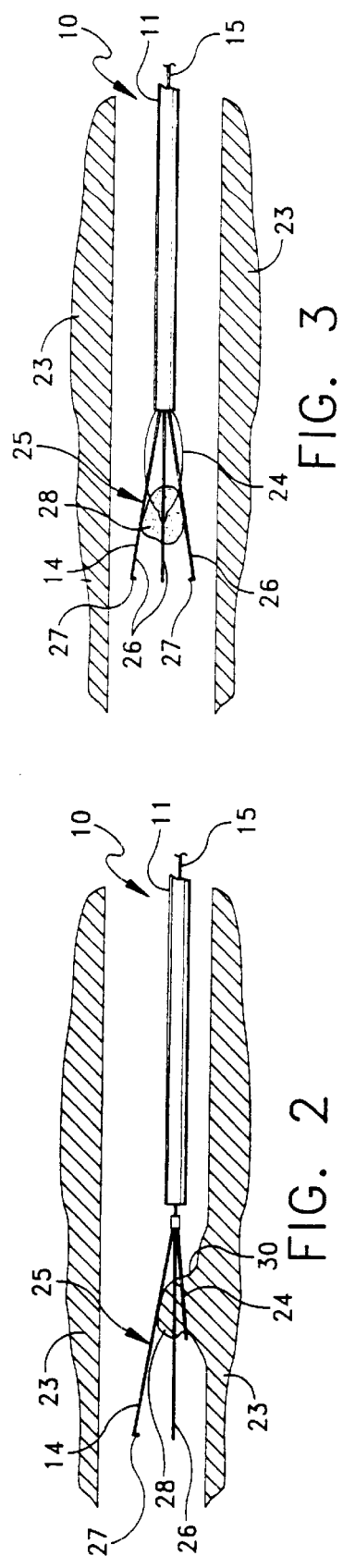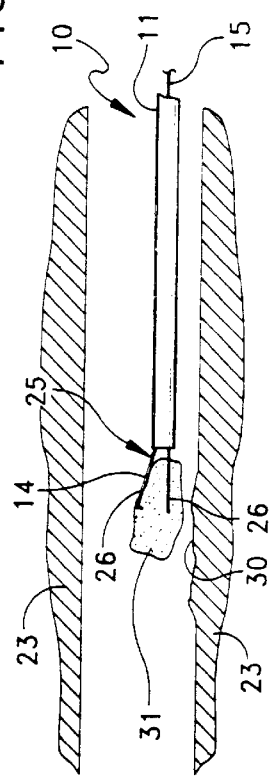

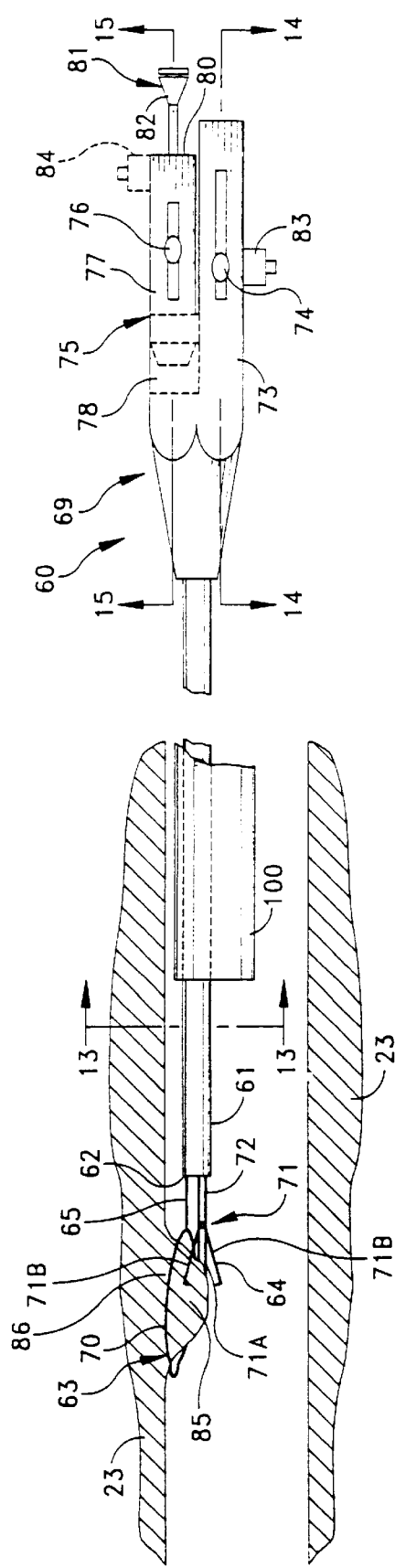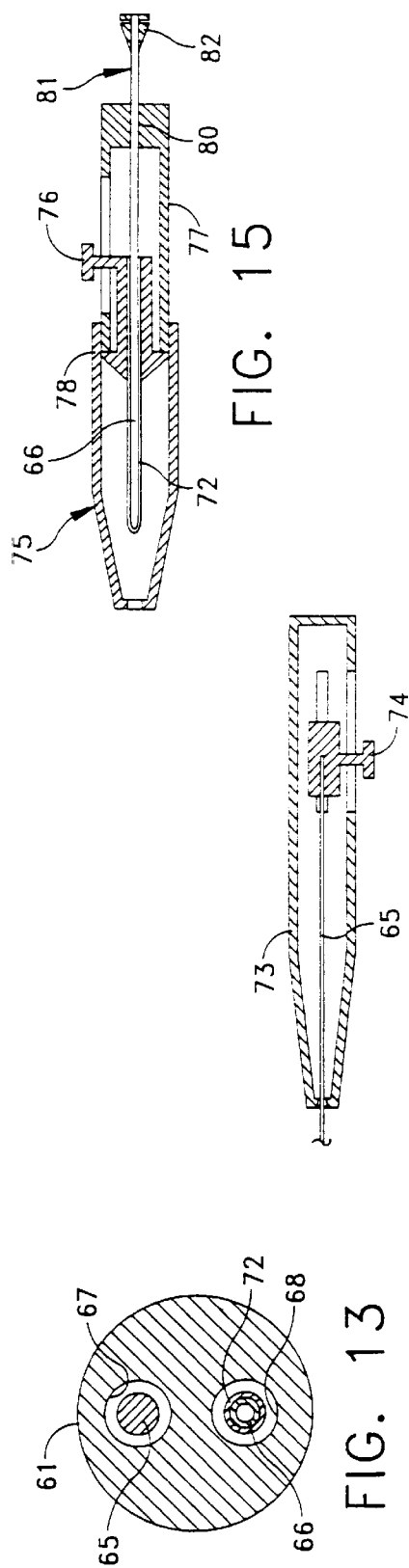

APPARATUS FOR SEVERING AND CAPTURING POLYPS

This is a continuation of application Ser. No. Pat. No 09/457,700, filed Dec. 9, 1999, now U.S. Pat. No. 6,171,315 which is a division of application Ser. No. 09/146,105, filed Sep. 3,1998, now Pat. No 6,010,512, which is a division of application Ser. No. 08/421,409, filed Apr. 13, 1995, now U.S. Pat. No. 5,846,248, all of which are incorporated herein by reference.

BACKGROUND OF THE INVENTION

1. Field of the Invention

This invention relates to surgical apparatus and methods for polyp management and more particularly to such apparatus and methods for severing and capturing polyps.

2. Description of Related Art

The treatment of polyps and other similar growths in a patient has improved greatly within the last several decades. Polyps are generally collected for histopathological evaluation to determine if they are cancerous. Initially the primary method of treating polyps was major surgery. Now polypectomy procedures are based upon the insertion of a surgical catheter through the working channel of an endoscope. Polypectomy procedures have essentially replaced surgical procedures except when polypectomy procedures are deemed unsuitable, such as when the polyp or polyps to be removed are relatively planar in nature. As used in this application, an endoscope includes endoscopic or other similar device that is inserted into a patient and that includes a working channel for receiving a surgical catheter or the like and a viewing channel for viewing the interior of a vessel.

The following United States Letters Patent disclose surgical apparatus for polyp management procedures:

U.S. Pat. No. 5,122,147 (1992) Sewell, Jr.
U.S. Pat. No. 4,326,530 (1982) Fleury, Jr.

Sewell, Jr. discloses several embodiments of a polyp marking device and method of using them. FIG. 4 illustrates three generally concentric loops extending from the distal end of the housing. Spacing members contact each loop thereby to position the loops along radially inner, outer and underneath paths. The inner loop 20 has one end fixed to the housing and rachets onto a polyp proximate its base by retraction of a second end extending distally through the housing. The outer loop 23 retracts to grasp the polyp proximate its free end. An intermediate cutting loop has one end fixed in the housing and severs the polyp by retraction of a second end extending through the housing. The inner loop 20 remains attached to the base of the severed polyp.

In another embodiment disclosed by Sewell, Jr. retraction of a cutting loop 21 severs an inner loop 20 from a housing. After such retraction, a forceps device is inserted through the distal end of the housing. Manipulation of the forceps device enables a physician to capture the severed portion of the polyp. Other embodiments disclosed by Sewell, Jr. disclose clamping devices or jaws having one or more cutting edges for severing a polyp whereby the jaws close to return the severed portion of the polyp. Sewell, Jr. avoids the use of an electric current for cauterizing the severed base by applying a hemostatic agent to the base of the polyp from the inner loop.

Fleury, Jr. discloses a surgical instrument for removing cellular tissue from body cavities. The instrument includes a proximal handle and a distally extending tubular member. A cable passes through the tubular member and includes a self-expanding loop or snare at its distal end. Extension and retraction of the cable enables the loop to enlarge and encompass a polyp and then contract to and sever the polyp. The loop conducts rf electrical current to cauterize the stump of the severed polyp. However, the catheter of Fleury, Jr. does not provide apparatus associated with the instrument itself for capturing the severed portion of the polyp. Rather Fleury, Jr. suggests that other suitable means such as suction associated with a colonscope equipment (i.e., an endoscopic device) captures the severed portion.

Another type of known surgical catheter for performing polypectomy procedures includes a loop or snare disposed at the distal end of the catheter. A basket or net connects to the loop along its defined arc. In use the basket overlies the portion of a polyp to be severed by the loop. Thus, upon severing of the polyp the basket captures the severed portion.

The advantages of such prior art polypectomy procedures in contrast to major surgery are numerous. The advantages generally include reductions in the time and trauma of the operation itself, the time of recovery of the patient, the risk of infection and other problems associated with major surgery. Thus, a surgical catheter device of the prior art generally includes a tubular member extensible through the working channel of an endoscopic device with a cutting loop positioned at the distal end of the tubular member and may include a mechanism for cauterizing the base of a severed polyp.

However, prior art polypectomy devices sometimes are unsuitable for treating certain polyps and are cumbersome and often extend the duration of a procedure unnecessarily.

Some embodiments disclosed by Sewell, Jr., for example, require the use of a separate forceps instrument used in conjunction with the disclosed instrument to retrieve the severed polyp. Generally, Sewell, Jr. discloses a device which requires multiple control wires, three wires in the case of the embodiment of FIG. 4. Furthermore, Sewell, Jr. leaves the inner loop within the body of the patient so that it must be retrieved or otherwise passed from the patient's body.

The device disclosed by Fleury, Jr. also has limited usefulness because it does not include any apparatus for grasping the severed portion. Although some endoscopic devices use suction to extract tissue, the suction, at acceptable levels, is frequently insufficient to hold a severed polyp at the end of the device. Using suction also requires positioning the distal end of the endoscope proximate the polyp. This is not always a simple task. It frequently requires a high degree of skill and dexterity. Should the polyp not be held, it is often difficult to retrieve the severed polyp. Using a forceps device to retrieve such severed portion usually requires the removal of the surgical catheter from the working channel of the endoscope device and insertion of the forceps device. The snare and basket arrangements offer the possibility of retrieving several polyps without removing the apparatus from a patient. However, the weight of the basket depending from the snare tends to deflect the snare and the distal end of the surgical instrument. Consequently it can be difficult to maneuver the snare over a selected polyp. The loops of the basket overlying the snare also can impede snare closure and severance of a selected polyp. Moreover, the movement of the basket loops along the snare tends to dull the snare and makes the severing more difficult. The baskets, being metallic, can contact the snare and bypass current used for cauterizing the severed stump of the polyp. Also, in the case where multiple polyps are collected there is no means to adequately associate the particular polyps collected with the location from which such polyps were taken.

The prior art taken collectively, thus fails to provide an easily used and simply constructed surgical apparatus for effectively and reliably severing and capturing polyps at diverse shapes and sizes. There is no suggestion of a method and apparatus for efficiently and effectively capturing a polyp or severing and capturing successive ones of such polyps in a reliable manner and, additionally, being able to associate the position from which such polyps were taken with particular polyps. Further, the prior art devices which require repeated removal and insertion to take a plurality of polyps generally also require repeated removal and insertion of the endoscope, because polyps frequently are larger than the working channel of such endoscopes. Thus, the repeated insertion and removal increases the time for such polypectomy procedures and associated trauma to the patient.

SUMMARY

Therefore, it is an object of the present invention to provide a surgical apparatus for effectively and reliably severing and capturing a polyp.

Another object of this invention is to provide a surgical apparatus that is simple to manufacture and use and that efficiently and effectively captures and severs a polyp.

Still another object of this invention is to provide a method for managing polyps that enables a physician to efficiently and effectively remove polyps from a patient.

Yet another object of this invention is to provide a surgical apparatus having a holding device and a severing device positioned at a distal end of the apparatus that are independent of each other.

Yet still another object of this invention is to provide a surgical apparatus having a control mechanism for concurrent extension and retraction of a holding device and a severing device positioned at a distal end of the apparatus.

Still yet another object of this invention is to provide a method for severing and capturing a polyp that includes the step of positively holding the polyp prior to severing such that the severed portion of the polyp is captured.

Yet a further object of this invention is to provide a method and apparatus for enlarging a polyp to promote severing and for capturing a polyp.

Still yet a further object of this invention is to provide a method and apparatus for successive severing and capturing of polyps within a patient prior to removal of the apparatus.

A further object of this invention is to provide a method and apparatus for retaining severed and captured polyps in an order corresponding to the order of such severing and capturing.

According to one aspect of this invention apparatus for severing and retaining a polyp includes an axially extending catheter with a distal end that can be positioned proximate a polyp. A self-expansible severing and capturing device is extensible from the distal end in an expanded form and is retractable into the catheter in a compacted form. Actuation of a control device at a proximal end of the catheter externally of the patient enables extension and retraction of the severing and capturing device relative to the distal end of the catheter thereby to enable polyp removal.

According to another aspect of this invention a surgical instrument, adapted for use in the working channel of an endoscopic device and for capturing and severing a portion of a polyp, includes an elongated tubular member extending proximally from a distal end and a snare carried by the tubular member for encompassing and severing a polyp. Selective extension of a holding device carried by the tubular member independently of the snare holds the polyp proximate its free end so that upon severing of the polyp the holding device retains the severed portion of the polyp.

According to yet another aspect of this invention a surgical instrument for severing and capturing a polyp includes an elongated tubular member proximally extending from a distal end and adapted to extend through the working channel of an endoscopic device with a viewing channel. The tubular member supports a snare for extension in an enlarged condition and retraction in a compact condition relative to the distal end. Control apparatus enables a physician to selectively extend and retract the snare. A capturing device connects with the control apparatus for extension and retraction with the snare so that upon retraction the capturing device grasps and retains a portion of the polyp severed by the snare.

According to a further aspect of this invention a method for managing polyps in a patient includes locating a catheter proximate a selected polyp. Extension of a self-expansive severing device from the catheter encompasses the polyp proximate its base. Extension of a holding device from the distal end of the catheter upon maneuvering engages the polyp proximate a free end thereof. Retracting the severing device into the catheter severs the polyp proximate the polyp's base; the holding device retains the severed portion that includes the free end.

According to yet a further aspect of this invention a method for managing polyps in a patient includes locating a catheter proximate a select polyp. Extension and orientation of a severing and holding device from the catheter includes encompassing the polyp with a severing portion of the device and a holding portion of the device engaging the polyp proximate a free end thereof. Retraction of the severing and holding device severs the polyp with the holding portion of the device retaining a separate portion including the free end of the selected polyp.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

FIG. 1 is a plan view of a surgical instrument constructed in accordance with this invention having a severing and holding device at a distal end portion for location within a patient proximate a polyp;

FIG. 2 is a enlarged side elevation of a distal end portion of FIG. 1;

FIG. 3 is a enlarged plan view of the distal end portion of FIG. 1 with the severing and holding device in partially retracted position;

FIG. 4 is a enlarged plan view of the distal end portion of FIG. 1 with the severing and holding device in a retracted position with the polyp severed at is base and the severed portion retained by the holding device;

FIG. 12 is a side elevation of a yet another surgical instrument constructed in accordance with this invention with a severing device and a holding device in an extending position relative to a tubular member;

FIG. 13 is a cross-section of the tubular member of FIG. 12 taken along the line 13—13;

FIG. 14 is a cross-section of the handle portion of FIG. 12 taken along the line 14—14;

FIG. 15 is a cross-section of the handle portion of FIG. 12 taken along the line 15—15;

DESCRIPTION OF ILLUSTRATIVE EMBODIMENTS

Figure 5:
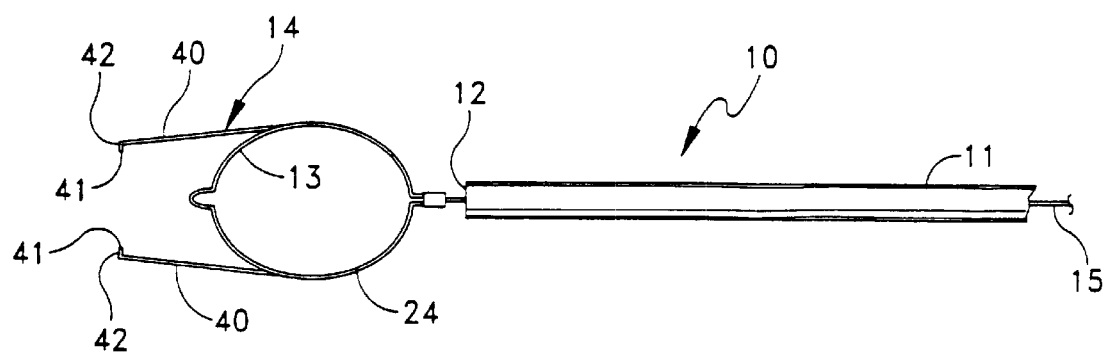
FIG. 5 is an enlarged plan view of the distal end portion of another surgical instrument in accordance with this invention.

As depicted in FIG. 1, apparatus 10 for managing polyps according to this invention includes a radially flexible, axial stiff elongated catheter or tubular member 11 extending proximally from a distal end 12 with a severing device 13 and a capturing device 14 extensible from and retractable relative to the distal end 12. The severing device 13 and the capturing device 14 connect at their proximal ends to a cable 15 that extends through the catheter 11 to a handle 16. The cable 15 in this embodiment connects to a slide member 17 suitably supported in the handle 16, although alternatively the cable can be fixed to the handle 16 with the slide member 17 connecting to the tubular member 11. Those skilled in the art will appreciate that displacement of the slide member 17 enables a user to selectively control the distal extension and proximal retraction of the severing device and the capturing device relative to the distal end 12.

FIGS. 1 through 4 illustrate the use of the present invention which is preferably used with a known endoscopic device having a working channel and a viewing channel. The severing device 13 in this embodiment is formed as a snare 24, and the capturing device 14 comprises forceps 25 with distally extending legs 26 secured to the snare extending from the distal end of the cable 15. Each of the legs 26 includes an inwardly extending portion 27 at its free or distal end.

In use, a physician inserts the distal end 12 through the working channel of an endoscope and uses the viewing channel to position the distal end 12 proximate a polyp 28. Once the severing and capturing devices 13 and 14 are extended relative to the distal end 12, the physician maneuvers the severing device 13 to encompass the polyp 28 proximate its base 30. The proper maneuvering of the severing device also positions the capturing device 14 as illustrated in FIGS. 1 and 2. The physician then retracts the cable 15 relative to the distal end 12 by moving the slide member 17 (FIG. 1) from its distal position toward the position 17' to displace the severing and capturing device 13 and 14 into the tubular member 11. As depicted in FIG. 3, retraction of the severing device 13 and the capturing device 14 causes the severing device 13 to close and sever a portion 31 of the polyp 28 and concurrently to urge the severed portion 31 into engagement between the legs 26. Thus, after the severing of the polyp 28 the severed portion 31 is retained by the capturing device 14 so that it can be removed from the patient as the tubular member 11 is withdrawn.

Figure 6:
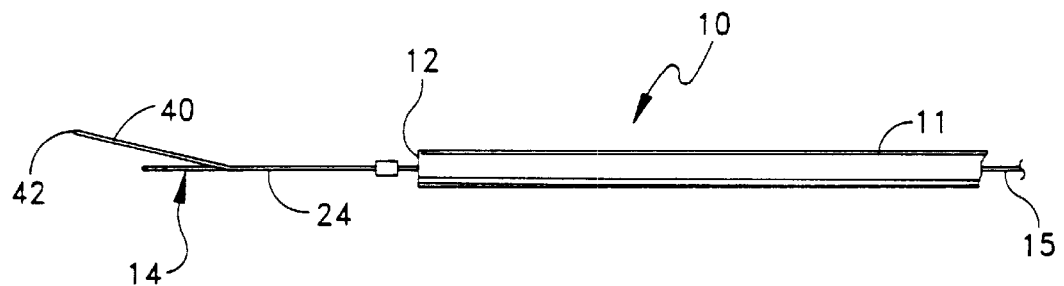
FIG. 6 is an enlarged side elevation of the distal end portion of the embodiment of FIG. 5.

FIGS. 5 and 6 depict an alternative embodiment including a severing device 13 and a capturing device 14. In this case the capturing device 14 comprises two leg members 40 extending from opposed central portions of the snare 24 to define a plane intersecting the plane of the snare 24. Retraction of the severing device 13 and the capturing device 14, once positioned so that the severing device 13 encompasses a polyp 28 with the capturing device 14 disposed proximate the free end of the polyp 28, urges the leg members 40 toward each other so that the portion 31 of the polyp 27 to be severed from the base 30 is grasped or gripped by the leg members 40 enabling retention and removal of the polyp from the patient. Each of the leg members 40 may also include a radially inwardly extending projection 41 proximate free ends 42 to capture the severed portion 31 in a positive fashion.

Figure 9:
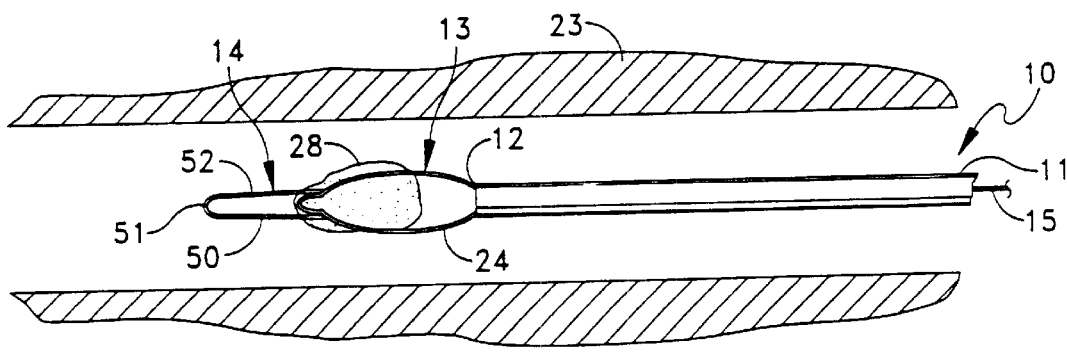
FIG. 9 is a plan view of the embodiment of FIG. 7 with the severing and holding device in a partially retracted position.
Figure 10:
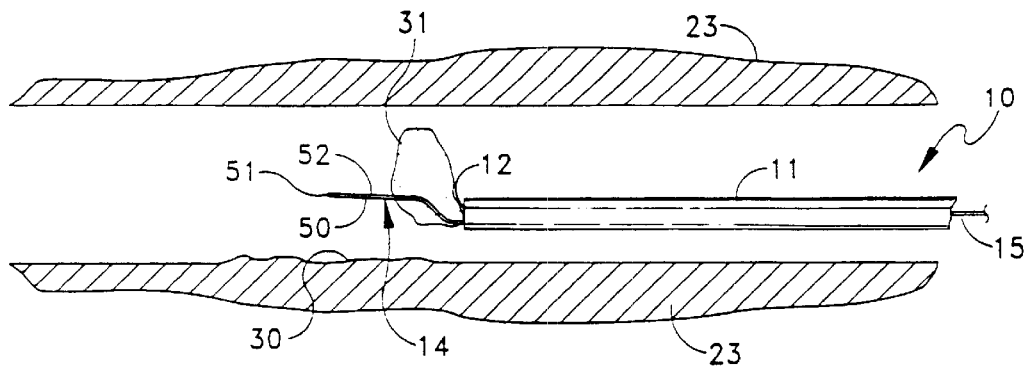
FIG. 10 is a plan view of the embodiment of FIG. 7 with a severing portion of the severing and holding device retracted into the tubular member.
Figure 11:
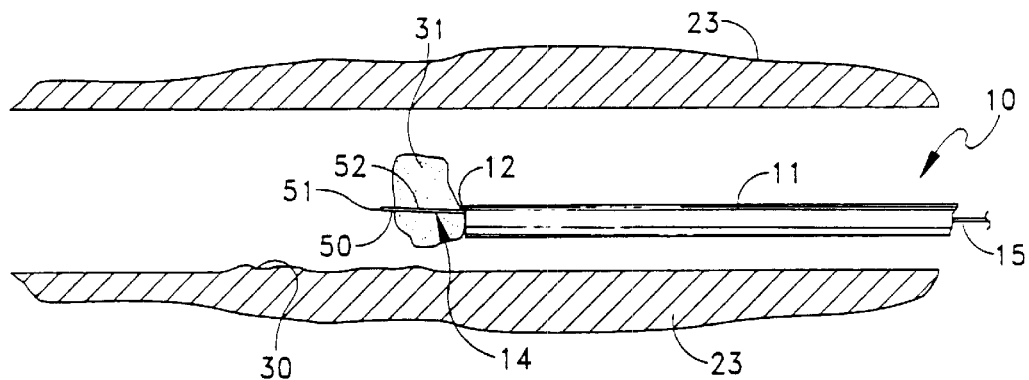
FIG. 11 is a plan view of the embodiment of FIG. 7 with the distal portion of a holding portion of the severing and holding device retracted proximate the distal end of the tubular member.

FIGS. 7 through 11 depict another embodiment of this invention that includes a severing device 13 and a capturing device 14 that are formed as a snare 24 and a collar or clip 50, respectively. The clip 50 has a closed distal end 51 with legs 52 extending proximally therefrom. The legs 52 attach to opposed central portions of the snare 24 so that the clip lies outside the plane defined by the snare 24. In using this embodiment, a physician positions the snare 24 to encompass a polyp 28 proximate its base and the clip 50 opposite the base 30 of the polyp 28. Retraction of the snare 24 into the tubular member 11, as depicted in FIGS. 9 and 10, severs the polyp 28 and urges the severed portion 31 into the clip 51. Further retraction, as depicted in FIG. 11 urges the severed portion 31 into a secure position against the distal end of the clip 51. It will be appreciated by those skilled in the art that providing a collar or clip of sufficient distal extension for receiving a plurality of polyps will enable the removal of such polyps prior to removal of the apparatus 10 from the patient's lumen 23.

Figure 7:
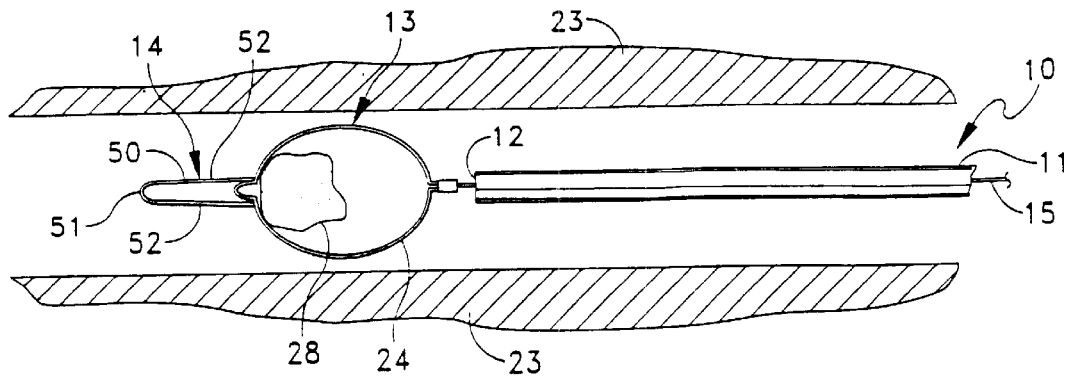
FIG. 7 is an enlarged plan view similar to FIG. 5 of the distal end portion of another surgical instrument in accordance with this invention.
Figure 8:
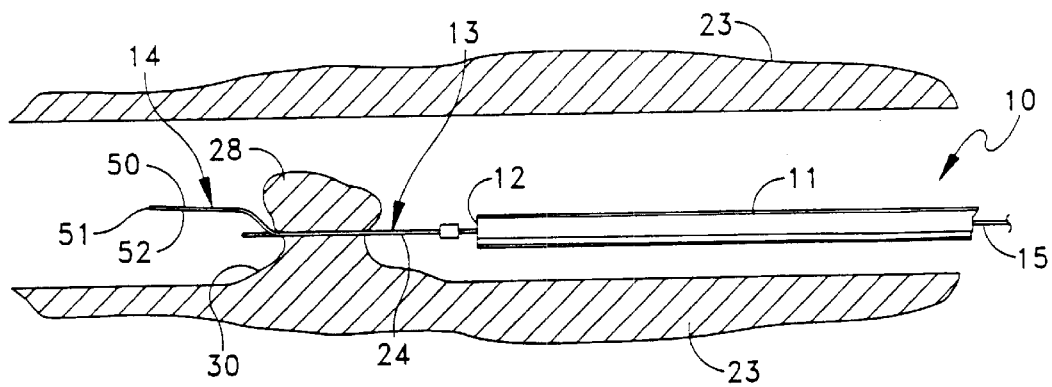
FIG. 8 is a side elevation of the distal end portion of FIG. 7.
Figure 11A:
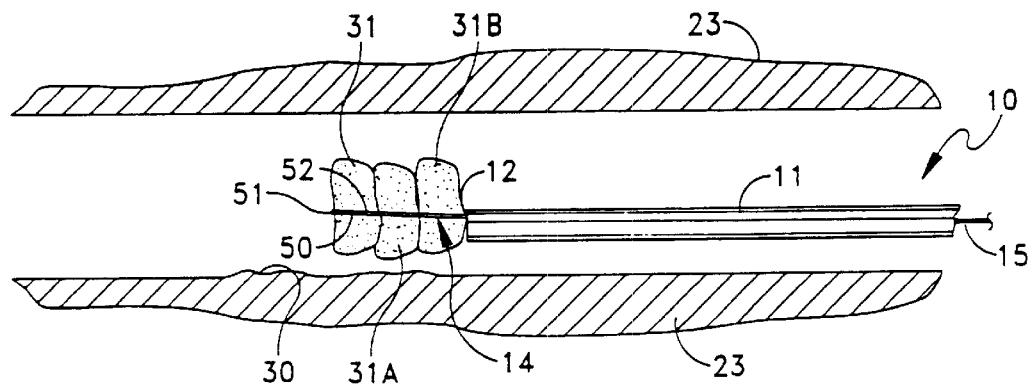
FIG. 11A is a view of the embodiment of FIG. 7 similar to FIG. 11 with the distal portion of the holding portion having a plurality of severed polyps retained therein.

The embodiment of FIG. 7 thus enables the grasping and retention of a plurality of polyps. The plurality of retained polyps will be arranged sequentially with the distal most polyp corresponding to the first sample sequentially with the proximal most polyp being the last polyp captured. Thus, the polyps will be stacked in the clip in the order of severing. Specifically each polyp is urged distally in the clip 50, as the cable 15 is retracted to bring the distal end 51 of the clip 50 proximate the distal end 12 of the tubular member 11. Thus, as illustrated in FIG. 11A where severed polyps 31 and polyps 31A and 31B have been sequentially severed and retained, the polyps 31, 31A and 31B would reside between the legs 52 in a secure position at the distal end 51 of the clip 50.

Use of this embodiment enables the physician to associate the polyps with the position from which it was severed. Thus, for example, only a portion of the plurality of the captured polyps are found to be cancerous, this ability to determine the location can be used to determine what segments of the lumen 23 need to be surgically removed. Use of this embodiment also eliminates the waste of time involved in removing from the patient's lumen 23 the tubular member 11 and generally an associate endoscope through which the tubular member is extended to retrieve a severed polyp after each severing and capturing operation.

FIG. 12 depicts still another apparatus 60 according to this invention that comprises a radially flexible, axial stiff elongated catheter or tubular member 61 having a distal end 62 from which a severing device 63 and a capturing device 64 extend and retract. The severing device 63 and the capturing device 64 connect at their proximal ends to a cable 65 and a hollow cable or hypotube 66, respectively, that extend proximal through lumens 67 and 68 (FIG. 13) in the tubular member 61 to a two part handle 69. The severing device 63 comprises an expansible snare 70, the capturing device 64, and a forceps-needle combination 71 that extends through a sheath 72 and that includes a hollow needle 71A that conveys fluid into a polyp.

Figure 17:
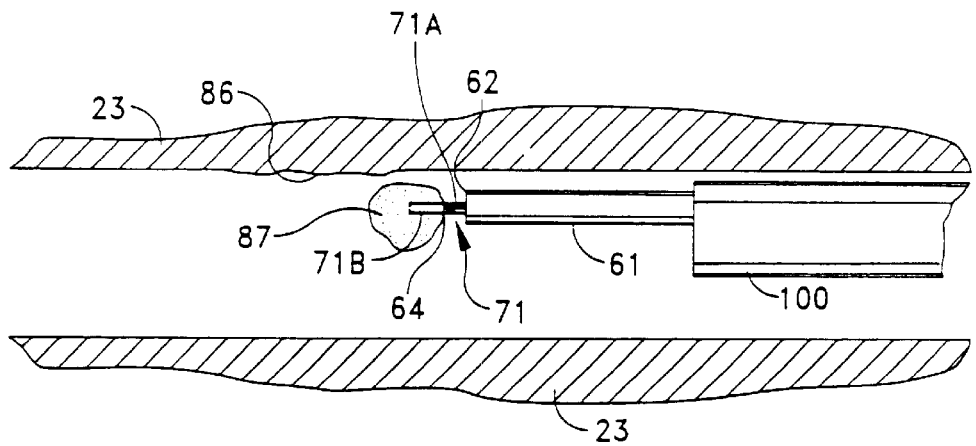
FIG. 17 is similar to FIG. 16 with the severing device retracted and the holding device retracted proximate the distal end of the tubular member.

Referring now to FIGS. 12, 14 and 15, a physician controls the operation of the forceps-needle combination 71 and the snare 70 from the handle 69 at a proximal end of the apparatus. A first portion 73 of the handle 69 (FIG. 14) supports a slider 74 that attaches to the cable 65. Distal displacement of the slider 74 enables the physician to extend the snare 70 from the distal end 62 as depicted in FIG. 12; proximal displacement of the slider 74 retracts the snare 70 as depicted in FIG. 17.

The handle 69 also includes an electrical plug 83 that suitably connects with the cable 65 to provide mono-polar cauterization of a base of a polyp severed by the snare 70. Alternatively, the electrical plug 83 can be eliminated in cases not needing cauterization or hypotube 66 can suitably connect plug 84 with the forceps needle combination 71 to enable bi-polar cauterization.

Figure 16:
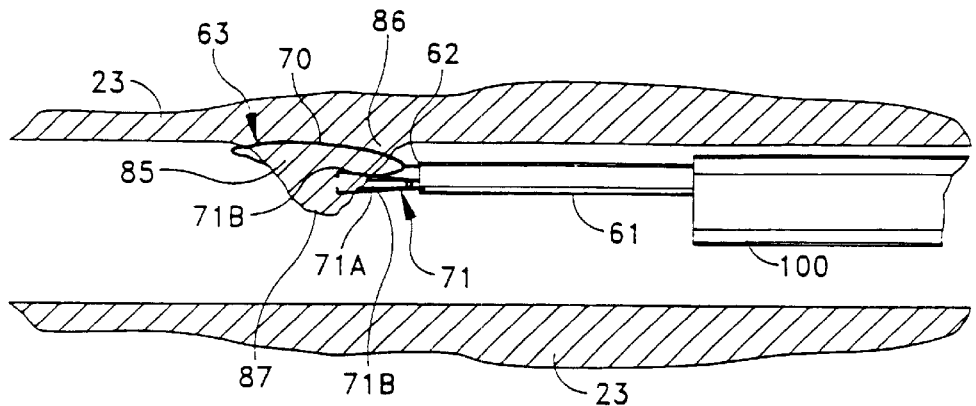
FIG. 16 is a side elevation of the distal portion of FIG. 12 with the holding device and the severing device partially retracted into the tubular member.

A second portion 75 (FIG. 15) of the handle 69 includes a slider 76 disposed in a slidable housing 77 supported in an outer housing 78 as depicted in cross-section in FIG. 15. The sheath 72 connects with the slider 76. Displacement of the slider 76, connected to sheath 72, relative to the slidable housing 77, connected to hypotube 66 and thus connected to capturing device 64, displaces the sheath 72 relative to the forceps-needle combination 71, thus enabling the extension, as depicted in FIG. 12, and retraction as depicted in FIG. 16. The hypotube 66 secures to a proximal end 80 of the slidable housing 77 so that displacement of the slidable housing 77 and the slider 76 together displaces the forceps needle combination 71 and the sheath 72 relative to the distal end 62 of the tubular member 61 (FIGS. 12 and 17). A proximal end 81 of the hypotube 66 in this embodiment includes an injection hub 82.

In operating the apparatus 60, the physician preferably positions the tubular member 61 to extend from the working channel of an endoscopic device 100 previously inserted in a patient. The physician manipulates the slider 74 and the slidable housing 77 and the slider 76 to extend the snare 70 and the forceps-needle combination 71 over a polyp 85, as depicted in FIG. 12. If the polyp 85 is a relatively small, flat polyp of a type that is usually difficult to sever and/or retrieve by prior art apparatus, the physician positions the snare 70 to encompass a base 86 of the polyp 85 and pierces the polyp 85 with the needle 71A between the base 86 and a free end 87 of the polyp 85 to inject a suitable fluid (e.g., a saline solution or sclerotherapy agents) into the polyp 85 from the injection hub 82 to expand and swell the polyp 85. The physician then closes forceps legs 71B of the forceps needle combination 71 to capture the now swollen polyp 85 by distal displacement of the sheath 72 relative to the forceps legs 71B (FIG. 16). Retraction of the snare 70 severs the polyp 85 so that the forceps-needle combination 71 retains the severed portion including the free end 87. Retracting the slidable housing 77 and distal displacing the slider 76, as shown in FIG. 17, moves the forceps-needle combination 71 into close proximity of the distal end 62.

Figure 18:
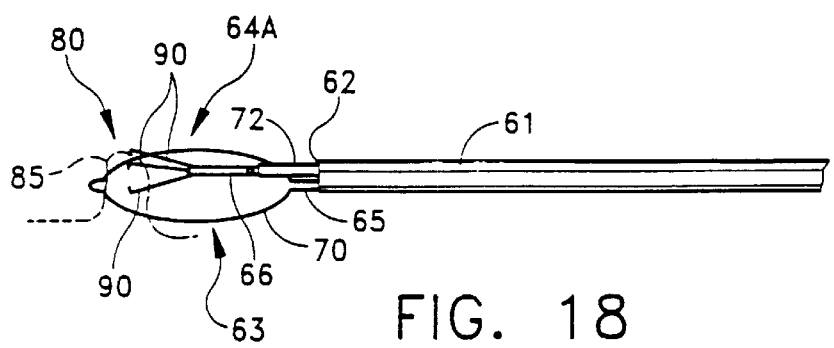
FIG. 18 is a perspective view of a distal portion of yet still another surgical instrument in accordance with this invention.
Figure 19:
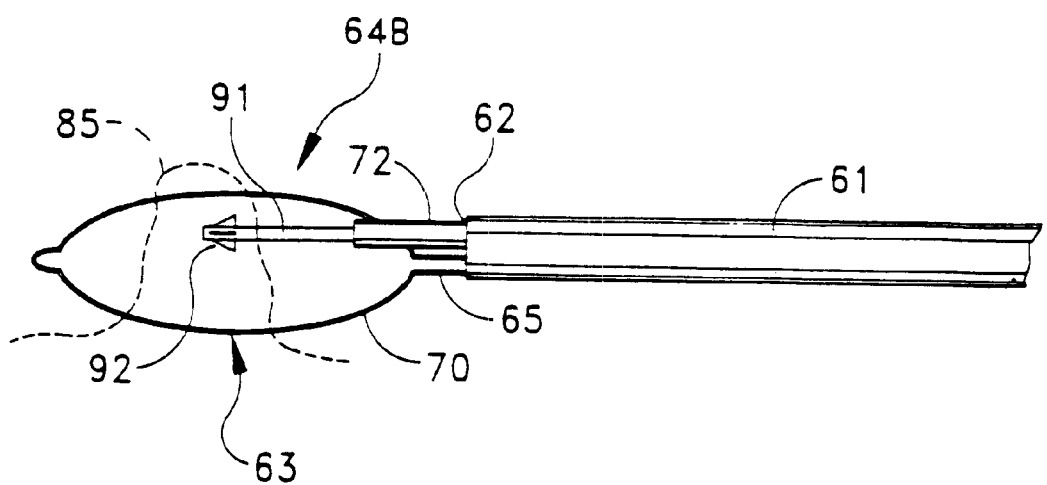
FIG. 19 is a perspective view of a distal portion of a further surgical instrument in accordance with this invention.

FIGS. 18 and 19 depict distal portions of the apparatus 60 with alternative capturing devices 64A and 64B, respectively. The embodiment of FIG. 18 includes only a forceps device 89 with extending legs 90. Those skilled in the art will understand that in this case the hypotube 66 can be solid and that the sheath 22 can, alternatively, be omitted so that the legs 90 expand and contract upon extension and retraction relative to the distal end 62 of the tubular member 61. Additionally, the hypotube 66 can be connected to a slider suitably mounted in a handle (not shown) similarly to the slider 74 of FIG. 12 with the slidable housing 77 of FIG. 12 also omitted.

The capturing device 64 of the embodiment of FIG. 19 includes only a needle 91 without any forceps device. The needle 91 operates substantially the same as the needle 71A of the embodiment of FIG. 12. That is, it connects with a proximal slidable member (not shown) to extend and retract the needle 91 and includes a means for enabling a fluid to be injected through the needle 91. The needle 91 further includes one or more barbs 92 or other similar surface features formed thereon proximate its distal end. The barbs 92 tend to retard withdrawal of the needle 91 from the polyp 85. Consequently, the polyp 85 tends to remain on the needle 91.

Figure 19A:
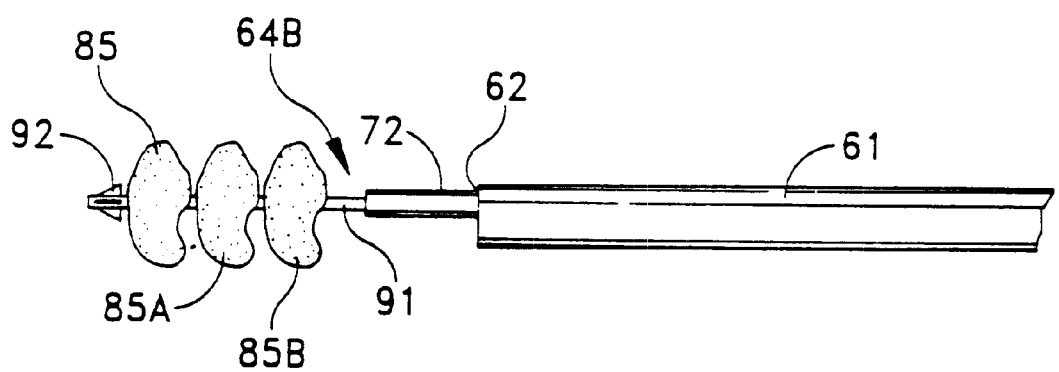
FIG. 19A is the view of FIG. 19 with a plurality of severed polyps retained on the retaining portion of the device and with the severing portion retracted.

Thus, after severing the polyp 85 by the snare 70, the severed portion polyp 85 including the free end 87 can be removed by withdrawal of the elongated tubular member 61. This embodiment also enables the collection of additional polyps by successively extending and positioning the snare 70 and needle 91 and then retracting the snare 70, as discussed above. That is to collect an additional selected polyp, such as the polyp 85 after collecting polyps 85B and 85A, respectively, the user positions the distal end of the device proximate the polyp 85 and extends the snare 70 to encompass the polyp and the needle 91 to pierce the polyp. Upon piercing the selected polyp 85, previously severed polyps retained on the needle 91 are urged proximally along the needle 91. The user can then inject the polyp 85 with a suitable solution, if desired, prior to severing the polyp 85 by retracting the snare 70. Once severed, the polyp 85 would be retained on the needle 91 as described above. Thus, as illustrated in FIG. 19A, a plurality of polyps severed and retained in the sequential order of the polyps 85B, 85A, 85 are retained proximate the distal end of the needle 91.

In summary, there have been described various embodiments of devices for severing and capturing polyps without prior art surgical intervention. Specifically, these devices include a catheter or like elongated tubular member having one or more lumens therein adapted for extending through the working channel of an endoscopic device having a viewing channel. Severing and capturing devices connect with control apparatus at the proximal end of the catheter to enable extension and retraction of the severing and capturing device relative to the distal end of the catheter. This structure enables a physician to selectively grasp a polyp, sever a portion of the polyp from its base and withdraw the polyp from the patient. The severing device typically includes a snare. The capturing device may comprise a closed end clip, legs arranged in a forceps-like configuration, a barbed needle, or combination thereof. A needle can also allow a physician to inject fluid into a polyp thereby to enlarge the polyp and facilitate its severing and its removal.

Those skilled in the art will further appreciate that the described devices can be relatively easily constructed according to known methods and relatively easily used by physicians familiar with prior art devices. However, this invention provides physicians with devices that are more versatile in dealing with polyps and that are relatively easily used while also providing greater surety in retention of the portions of polyps that are severed as compared with the prior art devices. This invention has been disclosed in terms of certain embodiments. It will be apparent that many modifications can be made to the disclosed apparatus without departing from the invention. Therefore, it is the intent of the appended claims to cover all such variations and modifications as come within the true spirit and scope of this invention.

What is claimed as new and desired to be secured by Letters Patent of the United States is:

1. An endoscopic instrument for severing and capturing a polyp from a patient, the instrument comprising:
    a catheter having a distal end and a proximal end;
    a first cable extending between said distal end and said proximal end of said catheter;
    a snare for severing the polyp from the patient, said snare being coupled to a distal end of said first cable and being at least partially extensible from and at least partially retractable into said distal end of said catheter;
    second cable extending between said distal end and said proximal end of said catheter;
    a self-expansible forceps for holding the severed polyp, said forceps being coupled to a distal end of said second cable and being at least partially extensible from and at least partially retractable into said distal end of said catheter, said snare and said forceps configured so that said forceps is capable of holding a portion of the polyp to be severed and removed while said snare severs the polyp;
    a needle for piercing the polyp, said needle coupled to said distal end of said second cable; and
    a control device coupled to said proximal end of said catheter for extending and retracting said snare and for extending and retracting said forceps and said needle relative to said distal end of said catheter.

2. The instrument of claim 1, wherein said needle is hollow and said second cable is hollow.

3. The instrument of claim 1, wherein said control device includes a first slider coupled to a proximal end of said first cable and slidably coupled to said control device and a second slider coupled to a proximal end of said second cable and slidably coupled to said control device.

4. An endoscopic instrument for severing and capturing a polyp from a patient, the instrument comprising:
    an elongate catheter having a distal end and a proximal end;
    a first flexible member extending through said catheter and having a distal end and a proximal end;
    a severing device coupled to said distal end of said first flexible member and being at least partially extensible from said distal end of said catheter;
    a second flexible member extending through said catheter and having a distal end and a proximal end;
    a self-expansible capturing device coupled to said distal end of said second flexible member and being at least partially extensible from said distal end of said catheter, said severing device and said capturing device configured so that said capturing device is capable of retaining the portion of the polyp to be severed and removed while said severing device severs the polyp;
    a needle coupled to said distal end of said second flexible member; and
    a control device coupled to said proximal end of said catheter, said proximal end of said first flexible member and said proximal end of said second flexible member, said control device capable of moving said severing device relative to said catheter and said capturing device relative to said catheter.

5. The instrument of claim 4, wherein said needle is hollow and said flexible member, which is coupled to said needle, is hollow.

6. The instrument of claim 4, wherein said severing device includes a snare.

7. The instrument of claim 4, wherein said capturing device includes a forceps.

8. The instrument of claim 4, wherein said control device includes a first slider coupled to said proximal end of said first flexible member and slidably coupled to said control device and a second slider coupled to said proximal end of said second flexible member and slidably coupled to said control device.

9. The instrument of claim 4, wherein an elongate sheath extends between said distal end and said proximal end of said catheter, said elongate sheath having a distal end and a proximal end, and said control device being coupled to said proximal end of said sheath and capable of moving said sheath relative to said catheter.

10. The instrument of claim 9, wherein said control device includes a first slider coupled to said proximal end of said first flexible member and slidably coupled to said control device, a second slider coupled to said proximal end of said second flexible member and slidably coupled to said control device, and a third slider coupled to said proximal end of said sheath and slidably coupled to said control device.

* * * * *